United States Patent [19]
Singo et al.

[11] Patent Number: 6,110,150
[45] Date of Patent: Aug. 29, 2000

[54] ENEMA EXTENSION

[76] Inventors: Ronald C. Singo; Janet L. Singo, both of 3985 Glades Pike, Somerset, Pa. 15501

[21] Appl. No.: 09/058,110

[22] Filed: Apr. 9, 1998

[51] Int. Cl.[7] .............................. A61M 5/178; A61M 5/00
[52] U.S. Cl. ............................................ 604/212; 604/117
[58] Field of Search ................................ 604/275, 30, 36, 604/37, 54, 55, 117, 328, 330, 73, 77, 212, 213; D24/111, 115

[56] References Cited

U.S. PATENT DOCUMENTS

| | | | |
|---|---|---|---|
| 120,525 | 10/1871 | Mattison | 604/275 |
| 286,041 | 10/1883 | Mayall | 604/275 |
| 826,172 | 7/1906 | Kintner | 604/275 |
| 1,015,895 | 1/1912 | Kelley | 604/275 |
| 1,092,684 | 4/1914 | Wilde | 604/275 |
| 1,115,908 | 11/1914 | Dees | 604/275 |
| 1,644,606 | 10/1927 | Pelphrey | 604/117 |
| 2,148,541 | 2/1939 | Dierker | 604/275 |
| 2,832,341 | 4/1958 | Stack | 604/54 |
| 2,848,997 | 8/1958 | Misket et al. | 604/275 |
| 2,881,760 | 4/1959 | McGiveran et al. | 604/275 |
| 3,144,021 | 8/1964 | Diaz | 604/275 |
| 3,459,175 | 8/1969 | Miller | 604/117 |
| 3,474,788 | 10/1969 | Corbin et al. | 604/275 |
| 3,486,503 | 12/1969 | Porter et al. | 604/275 |
| 3,575,160 | 4/1971 | Vass | 604/117 |
| 3,823,714 | 7/1974 | Waysilk et al. | 604/54 |
| 4,068,663 | 1/1978 | D'Alessandro | 604/275 |
| 4,519,794 | 5/1985 | Sneider | 604/279 |
| 5,125,914 | 6/1992 | Bassin | 604/275 |
| 5,447,496 | 9/1995 | Bove et al. | 604/54 |
| 5,496,268 | 3/1996 | Perla | 604/117 |
| 6,848,603 | 11/1974 | Throner | 604/54 |

*Primary Examiner*—Sharon Kennedy
*Attorney, Agent, or Firm*—Cohen & Grigsby, P.C.

[57] ABSTRACT

Generally, the present invention comprises an enema extension designed to fit onto existing enema application bottle designs. The extension connects a conventional enema applicator nozzle to a conventional enema bottle cap which seals the applicator nozzle to the enema bottle. The extension is preferably made of plastic and is of a length sufficient to allow the enema applicator nozzle to be inserted into the patient's rectum as the enema bottle is removed to a remote location for manipulation by the administering party.

16 Claims, 5 Drawing Sheets

ENEMA EXTENSION

FIELD OF THE INVENTION

The present invention relates to medical equipment designed to assist health care workers in providing an enema to patients, and in particular to an extension adapted for use with existing enema application devices to allow the delivery of an enema to patients occupying a supine or immobilized position.

BACKGROUND OF THE INVENTION

An enema is a common medical procedure whereby fluid is injected into the rectum of a patient in order to induce bowel movement. The need for such a procedure typically arises in patients suffering from certain physical ailments in which voluntary bowel control is impaired.

Medical equipment currently exists in the art for administering an enema to patients in need of this medical procedure. Typically this equipment consists of an enema squeeze bottle filled with the fluid intended to induce bowel movement, which is capped by a short applicator nozzle to be inserted into the patient's rectum. This type of conventional enema application device suffers a major disadvantage caused by the length of the applicator nozzle, in that the nozzle is too short to allow medical personnel to easily administer the enema to the patient who occupies a supine or immobilized position. The short length of the applicator nozzle gives rise to a lack of clearance between the patient's buttocks and the enema bottle, which makes manipulation of the applicator nozzle into the rectum difficult, causing discomfort to the patient.

The present invention solves this problem by extending the length of the applicator nozzle or alternately providing an extra length of tubing between the enema bottle and the applicator nozzle. This extra length allows the applicator nozzle to be inserted into the supine or immobilized patient's rectum as the enema bottle is removed to a remote location for manipulation by the administering party. In this way, administration of the enema is made more comfortable for the patient and easier for the medical personnel, since the flexible extension eliminates the need to manipulate the patient in order to apply the enema.

Since the enema extension of the present invention is designed to fit onto existing enema application bottle designs, the invention also provides a benefit to manufacturers as well as the hospitals, nursing homes, rehabilitation centers and other health care service providers which will use the invention, since no modification of existing enema application equipment is required.

The invention has particular use in the administration of enemas to patients who are forced into a supine position due to pelvic, cervical or femur fractures, patients in traction and the like. The invention also has use in the self-administration of enemas by patients, especially those with arthritis or obesity, since the extension allows the bottle to be brought between the legs to the front of the patient, thereby eliminating the need for the patient to reach behind his or her body to apply the enema. The invention also has particular use in the administration of postpartum enemas on patients with episiotomies since the enema applicator nozzle cap would not pass against the patient's incision line.

With prior art enema devices, self-administration in the knee chest position is next to impossible. The left side position is possible if the right hand is kept back oat the buttocks for squeezing the bottle. This is a stressful ordeal for many consumers. The consumer must place his body in contortion in order to maintain proper position and still manipulate the bottle. This problem is greatly evident for the elderly, arthritic and obese consumer. Some frustrated consumers will position themselves on a commode for the administration of such enemas but this position is not effective as the medicament is deposited only in the rectum and not at the locations necessary to provide relief.

With the proposed device the consumer can stand or be positioned on a commode to insert the tubing into the rectum via the anal opening to the proper depth. The tubing and bottle is then brought between the legs while the consumer lies down on his or her side in a relaxed manner to squeeze the bottle for administration of the medicament. After administration, the consumer gently pulls on the tubing to dislodge it from the rectum. Spillage, which would give rise to the danger of the consumer slipping and falling, is prevented when the device is attached to a closed bottle. Additionally, no assembly of the device is required of the consumer.

The enema device of the present invention is designed to provide safety, proper convenience and versatility to the consumer in self administration of an enema. The length of the device eliminates the frustration of reaching back to the anus, and allows for proper administration. Additionally, the device does not require a dilator, and the optional inclusion of a depth indicator allows for proper depth insertion as well as deeper insertion if necessary. Because the consumer can use and feel the depth indicator, the risk of puncturing the colon is minimized. The device contains a removable anti reflux valve to allow the device to be utilized to administer gravity flow enemas. Plastic bottles, collapsible or not, are preferred for use in conjunction with the device because a plastic bottle is easier for the consumer to manipulate and the prevention of spills is decreased.

Accordingly, it is an object of the present invention to provide an enema extension adapted for use with existing enema application devices to allow the delivery of an enema to patients occupying a supine or immobilized position.

It is a further object of the present invention to provide an enema extension which allows the enema applicator nozzle to be inserted into the supine or immobilized patient's rectum as the enema bottle is removed to a remote location for manipulation by the administering party.

It is a further object of the present invention to provide an enema extension which permits administration of the enema to be made more comfortable for the patient and easier for the medical personnel by eliminating the need to manipulate the patient in order to apply the enema.

It is a further object of the present invention to provide an enema extension designed to fit onto existing enema application bottle designs.

It is a further object of the present invention to provide an enema extension which requires no modification of existing enema application equipment for use.

SUMMARY OF THE INVENTION

Generally, the present invention comprises an enema extension designed to fit onto existing enema application bottle designs. The extension is formed by extending the length of a conventional enema applicator nozzle, or by alternately providing an extra length of tubing between the enema bottle and the applicator nozzle to connect the applicator nozzle to a conventional enema bottle cap which seals the applicator nozzle to the enema bottle. The extension is preferably made of plastic and is of a length sufficient to allow the enema applicator nozzle to be inserted into the patient's rectum as the enema bottle is removed to a remote location for manipulation by the administering party.

Other advantages of the present invention will become apparent from a perusal of the following detailed description of a presently preferred embodiment when taken in connection with the accompanying drawings.

DETAILED DESCRIPTION OF THE PRESENTLY PREFERRED EMBODIMENT

Figure 1:
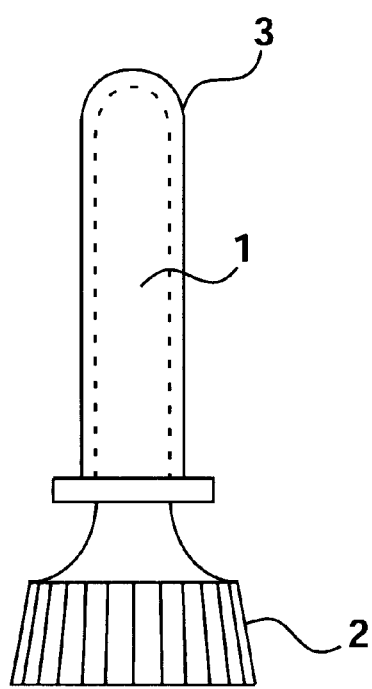
FIG. 1 is a sectional elevation view of a conventional enema applicator nozzle.
Figure 2:
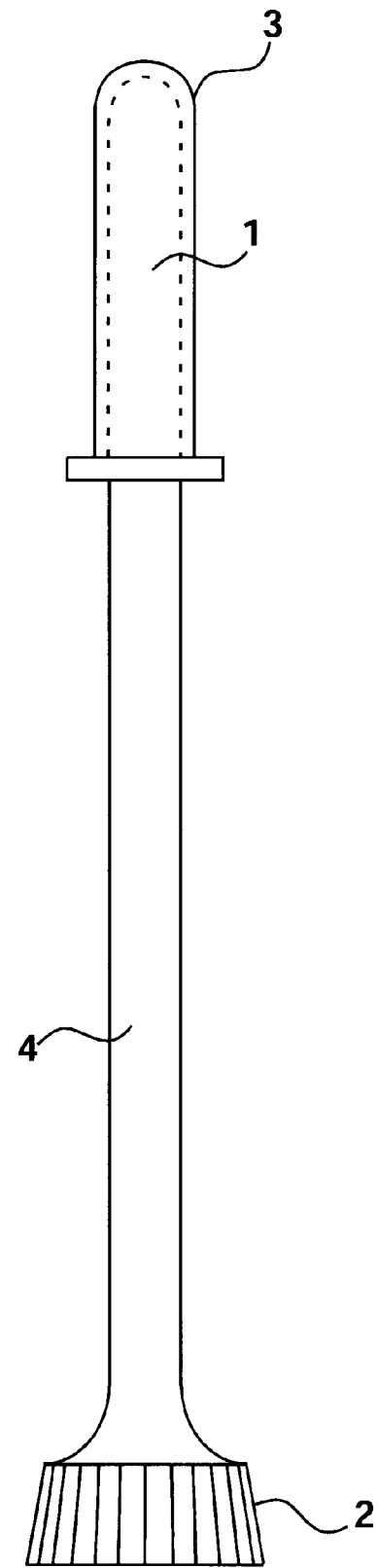
FIG. 2 is a sectional elevation view of the enema extension of the present invention.
Figure 3:
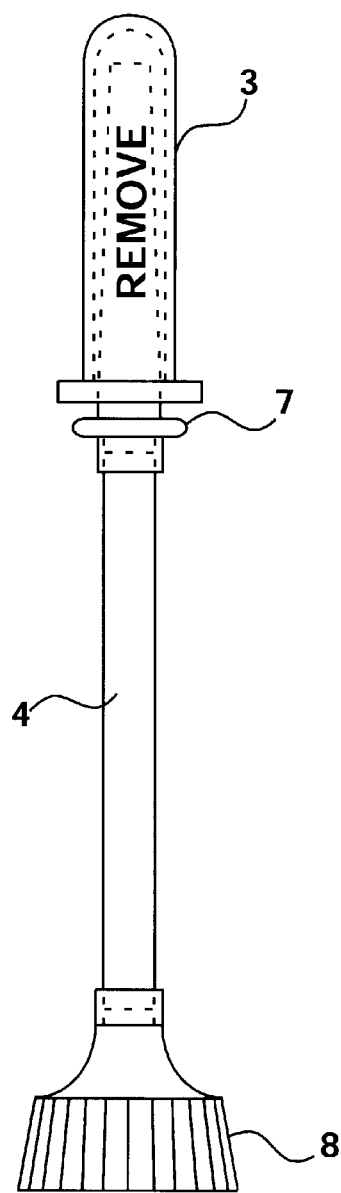
FIG. 3 is a sectional elevation view of the enema extension of the present invention as it appears complete.
Figure 4:
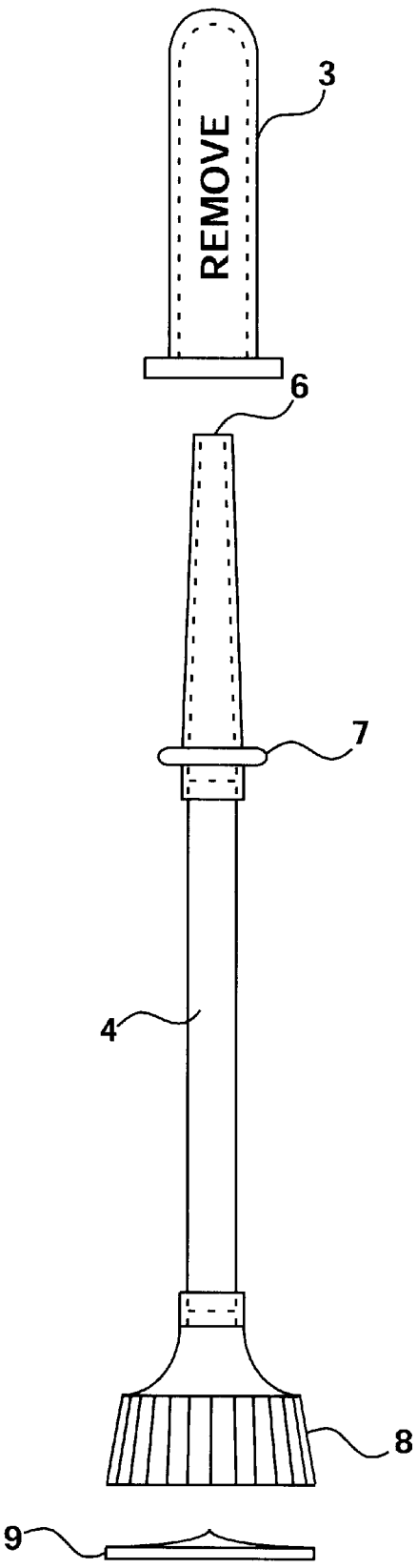
FIG. 4 is a sectional elevation view of the individual components of the enema extension of the present invention.
Figure 5:
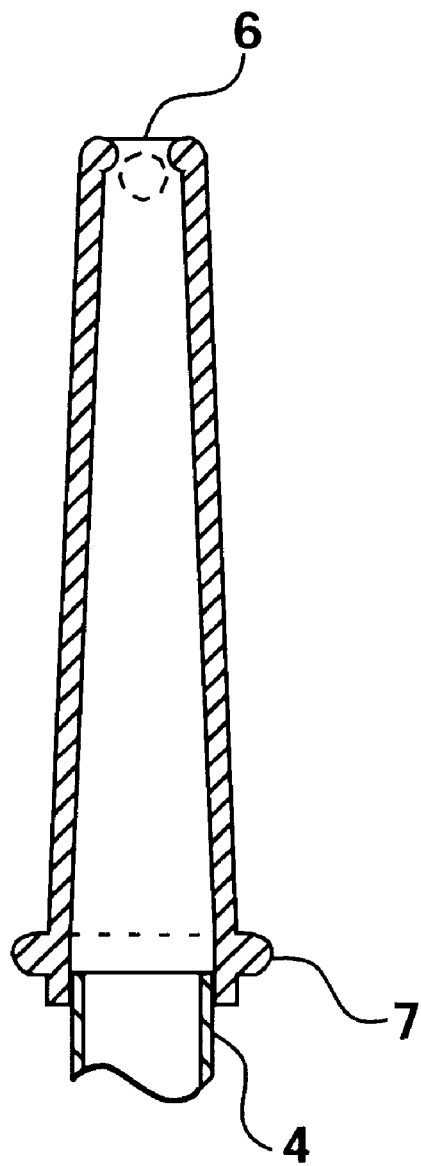
FIGS. 5A and 5B are cut away views of the protective cap and tubing of the enema extension of the present invention.
Figure 6:
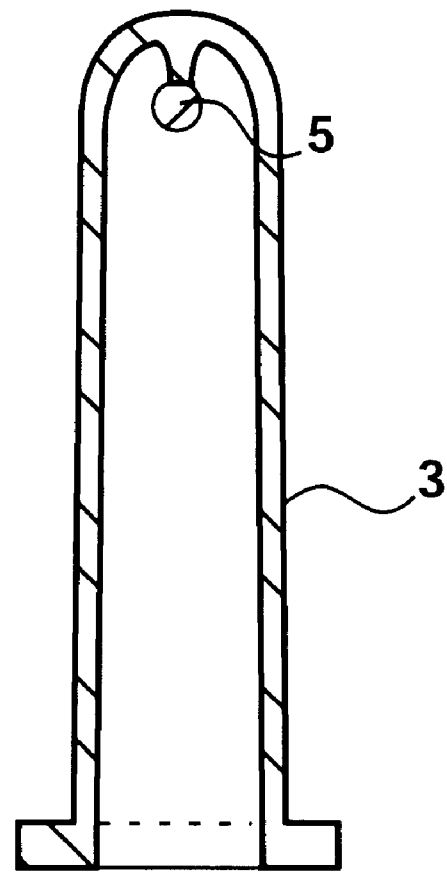
FIGS. 6A and 6F are views of the screw cap from its proximal end and its distal end showing the anti reflex valve of the enema extension of the present invention.
Figure 6A:
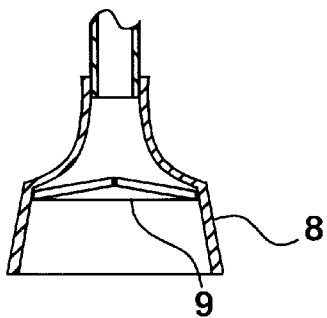
Figure 6C:
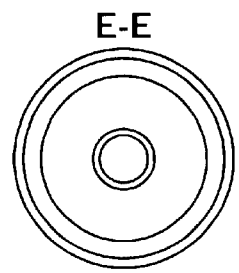
Figure 6E:
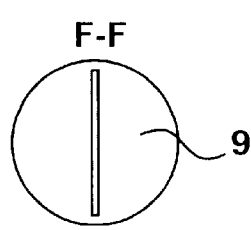
Figure 6B:
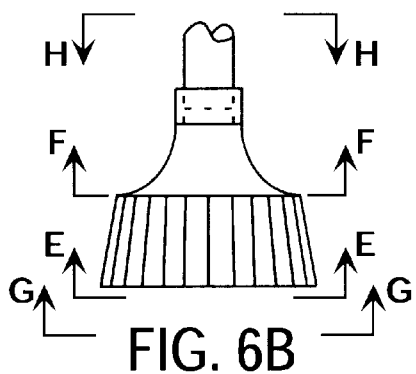
Figure 6D:
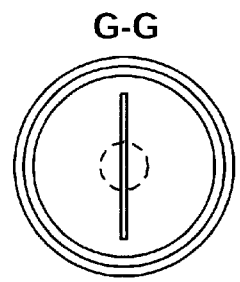
Figure 6F:
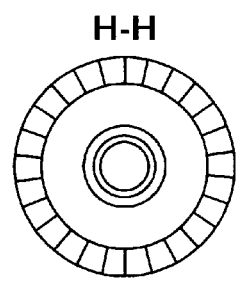
Figure 7A:
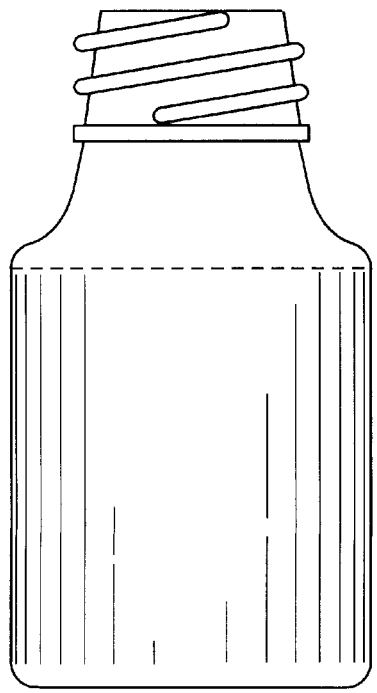
FIGS. 7A and 7B are commercial ready made plastic collapsible bottles in the upright and 180° turn position of the enema extension of the present invention.
Figure 7B:
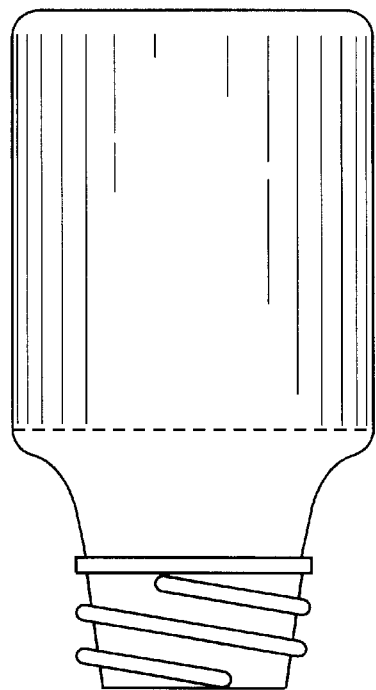
Figure 8:
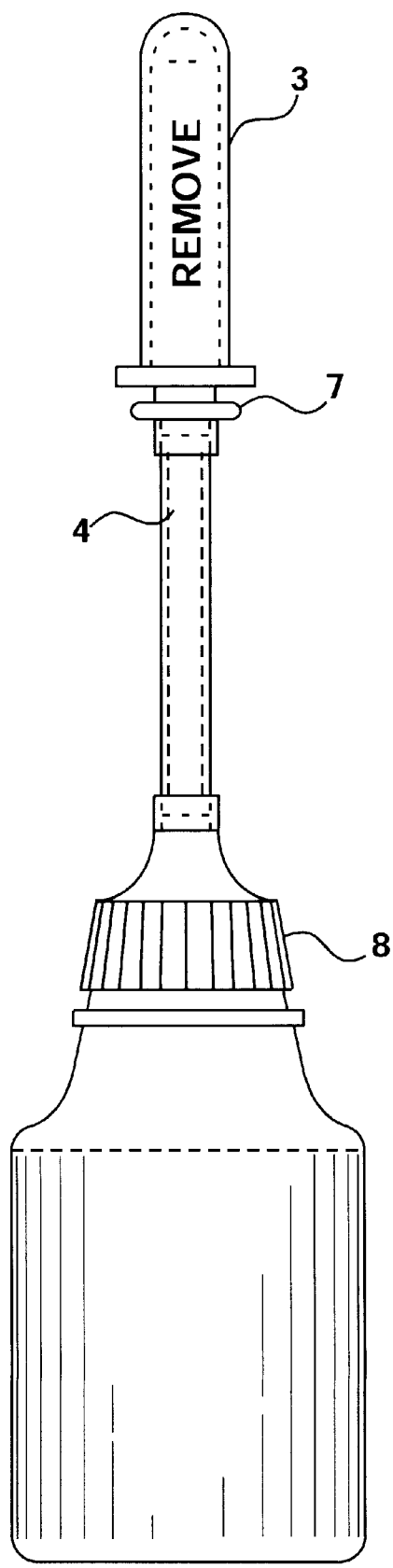
FIG. 8 is a view of the enema extension of the present invention as screwed to a ready made collapsible bottle.

A conventional prior art enema applicator nozzle 1 is shown in FIG. 1. Typically this conventional applicator nozzle 1 is not more than 2 inches in length and is secured to the enema bottle (not shown) by a conventional twist-on screw threaded bottle cap 2 which seals the applicator nozzle to the enema bottle. Typically the enema bottle cap 2 has a one-way safety valve, such as an anti-reflux valve, which prevents fluid which has escaped from reentering the enema bottle. The conventional applicator nozzle 1 typically has a lubricated tip and comes with a protective cover 3 which seals the interior of the nozzle from the environment. As stated above, the major disadvantage of a conventional enema applicator nozzle 1 such as that shown in FIG. 1 is that the nozzle is too short to allow medical personnel to easily administer the enema to the patient who occupies a supine or immobilized position. The short length of the applicator nozzle 1 gives rise to a lack of clearance between the patient's buttocks and the enema bottle, which makes manipulation of the patient necessary before the enema can be administered.

As shown in FIGS. 2 through 8, the enema extension 4 of the present invention is designed to connect a conventional applicator nozzle 1 to a conventional enema bottle cap 2. The extension is formed by extending the length of a conventional enema applicator nozzle 1, or by alternately providing an extra length of tubing between the enema bottle and the applicator nozzle to connect the applicator nozzle to a conventional enema bottle cap 2 which seals the applicator nozzle to the enema bottle. The extension 4 is preferably made of flexible soft plastic formed by conventional methods, such as blow molding or welding. When configured in the form of tubing, the extension 4 is of a larger diameter than either the applicator nozzle 1 opening or the bottle cap 2 opening, to allow a force fit at either end of the extension 4. The extension 4 is of a length sufficient to allow the applicator nozzle 1 to be inserted into the patient's rectum as the enema bottle is removed to a remote location for manipulation by the administering party. Typically, the length necessary for such remote manipulation is in excess of 12 inches.

The extension 4 consists of firm plastic protective cap 3 which has a nipple-like projection 5. This projection 5 secures the protection cap into the distal opening 6 of the extension 4 tubing. The projection 5 is approximately but not limited to 2¾ inches in length.

The extension tubing 4 is preferably at least 22" in length, but any length sufficient to allow self-administration of the enema is possible. The tubing 4 is hollow to allow for fluid flow of the medicament, with an inside diameter approximately (but not limited to) 3 millimeters. The outside diameter is approximately (but not limited) to 5 millimeters. The tubing 4 is made of material soft enough to be flexible but firm enough to maintain integrity for introduction into the anus.

The distal opening of the tubing end 6 is preferably smoothly rounded to prevent injury to the anus and lining of the rectal vault and colon. At a length from the distal open end 6 sufficient to permit the consumer to see what the proper depth of insertion into the anus should be (approximately 2 inches in the preferred embodiment) is the depth indicator 7. The depth indicator 7 is palpable with the fingers of the consumer so that during insertion he will be able to determine by touch when the proper depth of insertion has been obtained. Additional depth indicators 7 may be added at differing locations along the extension tubing 4 should consumer requests indicate a need. The depth indicator 7 is preferably made of the same material as the tubing, but can be made of any material which would not be harmful to the consumer, and is attached to the tubing by conventional techniques such as welding or blow molding. The depth indicator 7 encircles the tubing as a band, or annular ring, utilizing the full circumference of the tubing and has (but is not limited to) a thickness of approximately $\frac{1}{16}$–$\frac{1}{8}$ inch and has (but is not limited to) a width of $\frac{1}{8}$–$\frac{1}{4}$ inch. The depth indicator 7 does not prevent deeper insertion of the tubing into the rectum. Certain solutions utilized for enemas such as a soap and water enema requires a deeper depth of insertion if so ordered by the consumer's physician. Thus, the tubing can be advanced farther into the rectal vault if needed. The distal end of the extension tubing 4 between the distal end opening 6 and the depth indicator 7 is prelubricated, which along with the shape of roundedness at the distal end allows the tubing 4 to be self dilating. No dilatory device is required.

The proximal end of the extension tubing 4 is welded to a frigid plastic screw cap 8, which is shown in various views in FIGS. 6A to 6F. The screw cap is threaded to be compatible with the present day disposable saline enema's bottle shown in FIGS. 7A and 7B.

The screw cap contains a removable anti-reflux valve 9 which is located in the proximal end of the screw cap 8. Valve 9 preferably consists of a nonporous flexible material and can be circular in shape, and is of a size which permits accommodation into the cap 8 (preferably but not limited to approximately 1 millimeter in thickness). Preferably, the valve 9 is slightly beveled with a through and through slit across but not totally encompassing the circle at the diameter area. Valve 9 prevents reflux of the medicament back up into the bottle thereby holding back any contaminants as well as helping to sustain the collapsing ability of the bottle, and is readily removed from inside the screw cap by using the fingers.

Many hospital out patents testings require large volume (1000–2000 cc) enemas prior to testing. These enemas are done by the consumer at home before going to the hospital by using large volume medicaments introduced into the rectum by gravity flow. With the use of a large volume plastic bottle with compatible threading to this device, the reflux valve 9 can be removed from the screw cap 8 to allow the device to be used for gravity flow enemas. The bottle can then be pre-filled or sold empty and the medicament solution can be added by the consumer. Air displacement from the bottle can obtained by a very slight unscrewing of the screw cap while holding the plastic bottle at 180° position (shown in FIG. 7B). Such slight unscrewing prevents the leaking of the medicament solution.

The invention has particular use in the administration of enemas to patients who are forced into a supine position due to pelvic, cervical or femur fractures, patients in traction and the like. The invention also has use in the self-administration of enemas by patients, especially those with arthritis or obesity, since the extension allows the bottle to be brought between the legs to the front of the patient, thereby eliminating the need for the patient to reach behind his or her body to apply the enema. The invention also has particular use in the administration of post-partum enemas on patients with episiotomies since the enema applicator nozzle cap would not pass against the patient's incision line.

Finally, since the enema extension of the present invention is designed to fit onto existing enema application bottle designs, the invention also provides a benefit to manufacturers as well as the hospitals, nursing homes, rehabilitation centers and other health care service providers which will use the invention, since no modification of existing enema application equipment is required.

While presently preferred embodiments of the invention have been shown and described in particularity, it may be otherwise embodied within the scope of the appended claims.

What is claimed is:

1. An extension for use with an enema application device wherein said enema application device comprises at least a bottle, wherein said extension forms a nozzle to be inserted into a patient's rectum as said bottle is removed to a remote location for administration of said enema, and wherein said extension is connected to said bottle to permit said nozzle to be inserted into a patient's rectum as said bottle is removed to a remote location for administration of said enema; and further comprising an annular ring for indicating the depth of insertion of the extension during application of the enema and wherein said annular ring is insertable into the patient's rectum such that said annular ring permits insertion of the extension further into the patient's rectum than said indicated depth.

2. The extension of claim 1, further comprising a cap adapted for use with said extension to said bottle for sealing the contents of said bottle from exposure to said extension.

3. The extension of claim 2, further comprising a valve in communication with said cap for sealing the contents of said bottle from exposure to said extension.

4. The extension of claim 3, wherein said valve is a one-way valve.

5. The extension of claim 3, wherein said valve is removable from said cap.

6. The extension of claim 1, wherein said extension is comprised of plastic.

7. The extension of claim 1, wherein said extension is in excess of twelve inches in length.

8. The extension of claim 1, wherein said extension is formed from a method selected from the group consisting of blow molding and welding.

9. An extension in combination with an enema application device wherein said enema application device comprises at least a bottle, wherein said extension forms a nozzle to be inserted into a patient's rectum as said bottle is removed to a remote location for administration of said enema, and wherein said extension is connected to said bottle to permit said nozzle to be inserted into a patient's rectum as said bottle is removed to a remote location for administration of said enema; and further comprising an annular ring for indicating the depth of insertion of the extension during application of the enema and wherein said annular ring is insertable into the patient's rectum such that said annular ring permits insertion of the extension further into the patient's rectum than said indicated depth.

10. The combination of claim 9, wherein said application device further comprises a cap connecting said extension to said bottle for sealing the contents of said bottle from exposure to said extension.

11. The combination of claim 10, further comprising a valve in communication with said cap for sealing the contents of said bottle from exposure to said extension.

12. The combination of claim 11, wherein said valve is a one-way valve.

13. The combination of claim 11, wherein said valve is removable from said cap.

14. The combination of claim 9, wherein said extension is comprised of plastic.

15. The combination of claim 9, wherein said extension is in excess of twelve inches in length.

16. The combination of claim 9, wherein said extension is formed from a method selected from the group consisting of blow molding and welding.

* * * * *